(12) United States Patent
Wang et al.

(10) Patent No.: US 10,449,195 B2
(45) Date of Patent: Oct. 22, 2019

(54) PHARMACEUTICAL FORMULATION OF PALBOCICLIB AND A PREPARATION METHOD THEREOF

(71) Applicant: SHENZHEN PHARMACIN CO., LTD., Shenzhen (CN)

(72) Inventors: Zeren Wang, Shenzhen (CN); Jun Xu, Shenzhen (CN); Long Qu, Shenzhen (CN)

(73) Assignee: SHENZHEN PHARMACIN CO., LTD. (CN)

( * ) Notice: Subject to any disclaimer, the term of this patent is extended or adjusted under 35 U.S.C. 154(b) by 0 days.

(21) Appl. No.: 15/613,853

(22) Filed: Jun. 5, 2017

(65) Prior Publication Data

US 2017/0281631 A1    Oct. 5, 2017

Related U.S. Application Data (63) Continuation of application No. PCT/CN2016/086546, filed on Jun. 21, 2016.

(30) Foreign Application Priority Data

Mar. 29, 2016 (CN) .......................... 2016 1 0187046

(51) Int. Cl.
```
A61K 31/519    (2006.01)
C07D 471/04    (2006.01)
A61K 9/14      (2006.01)
A61K 9/16      (2006.01)
A61K 9/48      (2006.01)
```

(52) U.S. Cl.
CPC ............ *A61K 31/519* (2013.01); *A61K 9/146* (2013.01); *A61K 9/1652* (2013.01); *A61K 9/4808* (2013.01); *C07D 471/04* (2013.01)

(58) Field of Classification Search
CPC ........ A61K 31/519; A61K 9/48; A61K 9/146; A61K 9/1652; A61K 9/4808; C07D 471/04
See application file for complete search history.

(56) References Cited

U.S. PATENT DOCUMENTS

| | | | |
|---|---|---|---|
| 6,936,612 B2 | 8/2005 | Barvian et al. | |
| 7,208,489 B2 | 4/2007 | Barvian et al. | |
| 7,345,171 B2 | 3/2008 | Beylin et al. | |
| 7,456,168 B2 | 11/2008 | Barvian et al. | |
| 7,863,278 B2 | 1/2011 | Beylin et al. | |
| 8,557,995 B2 | 10/2013 | Miller et al. | |
| 2005/0019399 A1* | 1/2005 | Fischer ................. | A61K 9/0004 424/468 |
| 2007/0015802 A1* | 1/2007 | Lal ....................... | C07D 405/04 514/365 |
| 2009/0030005 A1 | 1/2009 | Kamb et al. | |
| 2011/0009353 A1 | 1/2011 | Chen-Kiang et al. | |
| 2014/0220112 A1* | 8/2014 | Szoka, Jr. ............ | A61K 31/194 424/450 |
| 2014/0309250 A1* | 10/2014 | Verma .................. | A61K 9/2027 514/275 |
| 2015/0111896 A1 | 4/2015 | Sharpless et al. | |
| 2015/0140036 A1* | 5/2015 | Mannick .............. | A61K 39/092 424/209.1 |
| 2015/0273070 A1 | 10/2015 | Li et al. | |

FOREIGN PATENT DOCUMENTS

| | | |
|---|---|---|
| CN | 101632668 A | 1/2010 |
| CN | 102106806 A | 6/2011 |
| CN | 104 434809 A | 3/2015 |
| CN | 104887641 A | 9/2015 |
| CN | 105816437 A | 8/2016 |
| WO | WO-03062236 A1 | 7/2003 |
| WO | WO-2005005426 A1 | 1/2005 |
| WO | WO-2010/055119 A2 | 5/2010 |
| WO | WO-2011/063309 A1 | 5/2011 |
| WO | WO-2014/011398 A1 | 1/2014 |
| WO | WO-2014128588 A1 | 8/2014 |
| WO | WO-2015/022609 A1 | 2/2015 |
| WO | WO-2015/160986 A2 | 10/2015 |
| WO | WO-2015/165571 A2 | 11/2015 |
| WO | WO-2016/015598 A1 | 2/2016 |
| WO | WO-2016/156070 A1 | 10/2016 |
| WO | WO-2016/193860 A1 | 12/2016 |

OTHER PUBLICATIONS

Rocca et. al., Expert Opinion on Pharmacotherapy, 2013, Taylor & Francis, vol. 15(3), pp. 407-420.*
W. Sun, et al. Impact of acid-reducing agents (ARAS) on the pharmacokinetics of palbociclib, a weak base with ph-dependent solubility under differing food intake conditions, European Journal of Cancer, (Dec. 31, 2015), S59.
International Preliminary Report on Patentability in corresponding PCT Application No. PCT/CN2016/086546, dated Jan. 11, 2017.
Babic, S. et al. Determination of pKa Values of active pharmaceutical ingredients. Trends in Analytical Chemistry, 26(11):1043-1061 (2007).
Huang, Y. et al. Fundamental aspects of solid dispersion technology for poorly soluble drugs. Acta Pharmaceutica Sinica B, 4(1):18-25 (2014).

* cited by examiner

*Primary Examiner* — Sarah Pihonak (74) *Attorney, Agent, or Firm* — Wilson Sonsini Goodrich & Rosati (57) ABSTRACT

The present invention belongs to the pharmaceutical field, and in particular, it relates to a pharmaceutical formulation of palbociclib and a preparation method thereof. The pharmaceutical formulation comprises palbociclib, an acidic auxiliary material, and optionally a hydrophilic high-molecular weight material, which has better solubility and in vitro dissolution property as compared with the conventional formulation and can be used for enhancing in vivo absorption and bioavailability of palbociclib.

8 Claims, 5 Drawing Sheets

PHARMACEUTICAL FORMULATION OF PALBOCICLIB AND A PREPARATION METHOD THEREOF

CROSS-REFERENCE TO RELATED PATENT APPLICATIONS

This application is a U.S. Continuation Application of the International PCT Application No. PCT/CN2016/086546, filed Jun. 21, 2016, and claims priority of Chinese Application No. 201610187046.8, filed Mar. 29, 2016 all of which are incorporated by reference in their entireties.

TECHNICAL FIELD

The present invention belongs to the pharmaceutical field. More specifically, the present invention relates to a pharmaceutical formulation of palbociclib and a preparation method thereof. The palbociclib of the present invention may be a palbociclib free base or any of its pharmaceutically acceptable salts.

BACKGROUND ART

World Health Organization statistics show that breast cancer is the world's second cause of cancer deaths in women. Over the past few decades, the incidence of breast cancer showed an increasing trend. It is expected that by 2020, there will be more than 1.7 million new cases of breast cancer each year. By 2012, there are 1.67 million new cases of breast cancer worldwide, accounting for 25% of all new cases of cancer, wherein 883,000 cases are in developed countries and 794,000 cases are in developing countries. The growth rate of new cases of breast cancer in developing countries is slightly higher than that in developed countries. There are 522,000 cases of breast cancer deaths, ranking fifth in lethality rate in all cancers. In underdeveloped areas, the breast cancer causes 324,000 women deaths, accounting for 14.3% of all cases of cancer deaths, and is the most frequent lethal cancer. In developed areas, there are 198,000 cases of breast cancer deaths in women, accounting for 15.4% of all cases of cancer deaths, second only to lung cancer. Therefore, breast cancer is still one of the world's important health problems.

According to the international patent WO2003/062236, palbociclib is an inhibitory agent for cyclin-dependent kinases (CDKs) 4 and 6, which inhibits the synthesis of DNA primarily by preventing cells from G1 phase to S phase via the inhibition of CDK4/6 activity, and can be used to treat metastatic breast cancer. Clinical trial studies have shown that palbociclib combined with letrozole is very effective in postmenopausal patients with locally infiltrating breast cancer or in newly diagnosed estrogen receptor (ER)-positive and HER-2-negative patients. Its chemical structure is as follows:

The structure and preparation method of said compound and its salts have been described in the international patent WO2003/062236 and U.S. Pat. No. 6,936,612. The preparation methods of free bases and salts of various acids are also described in the international patent application WO2005/005426 and U.S. Pat. Nos. 7,345,171 and 7,863,278. According to the description in the international patent application WO2005/005426, the solubility of the palbociclib free base in water is poor, which leads to a low bioavailability and is disadvantageous for the absorption in human body. The free base has a strong adhesive property upon impact, and said adhesive property is related to the specific surface area of the particles, so its particle size must be controlled in a certain range. According to the international patent application WO2014128588, it is necessary to use an active pharmaceutical ingredient (API) of palbociclib free base having a larger particle size in order to improve the physichemical properties and the capacity to produce a formulation product. If the palbociclib free base is reacted with an acid to generate salts so as to increase the solubility, the salts have a poor solid nature and thereby are disadvantageous for being developed as a solid formulation, according to the reports in the previously known patents.

At the same time, palbociclib is an insoluble drug. At present, palbociclib has been approved for sale in the United States. According to the instructions for the approved product of palbociclib in the United States, one of seven patients has poor absorption upon administration of the palbociclib product. For these patients, the efficacy of said product will be relatively low. It is likely that the poor solubility of the drug causes the poor absorption in some patients. Thus, in the present, it is very necessary to further improve the dosage form of palbociclib so as to increase the dissolution rate and bioavailability thereof.

SUMMARY OF THE INVENTION

It is an object of the present invention to develop a novel pharmaceutical product for improving the dissolution and bioabsorption of palbociclib. According to the prior art and common knowledge, it is generally considered that the in vitro dissolution of an oral solid formulation product of an insoluble drug has a certain correlation with its in vivo absorption. Thus, an in vitro dissolution method is employed in the present invention to assess the capacity of the formulation product to be absorbed in vivo.

The present invention has surprisingly found that the dissolution of the oral solid formulation product prepared by mixing the API of palbociclib with a pharmaceutically acceptable acidic auxiliary material and optionally adding another pharmaceutically acceptable excipient can be significantly increased relative to the oral solid formulation products prepared in the prior art.

The present invention has also surprisingly found that, the disadvantage that the API having a small particle size cannot be used for the preparation of formulations as disclosed in the international patent application WO2014128588 can be overcome by pulverizing the API of palbociclib to reduce its particle size to D90 at 20 μm or less and then mixing with a pharmaceutically acceptable acidic auxiliary material, or by mixing the API of palbociclib with the pharmaceutically acceptable acidic auxiliary material, co-pulverizing to reduce the particle size of the mixture to D90 at 20 μm or less, and optionally adding another pharmaceutically acceptable excipient; and after an oral dosage form is prepared, the in vitro dissolution can be significantly increased.

The present invention has also surprisingly found that the API of palbociclib and the pharmaceutically acceptable acidic auxiliary material can be co-dissolved in a solvent and the concentration of the API of palbociclib in the solvent can be up to 50 mg/ml or more; and when a hydrophilic high-molecular weight material is further added and dissolved evenly and the solvent is removed by volatilization, an amorphous solid dispersion is formed. After an oral solid formulation product is prepared by optionally further adding another pharmaceutically acceptable excipient, its dissolution is further significantly increased.

The present invention has also surprisingly found that the method for preparing a solid dispersion of the present invention can also convert the acidic auxiliary material into an amorphous state and the amorphous state can be maintained for a long period of time, which is advantageous for maintaining the amorphous state of the API of palbociclib.

In the invention, by adding the acidic auxiliary material, reducing the particle size of the API of palbociclib and making the palbociclib in an amorphous manner, the in vitro dissolution of palbociclib is increased, and thereby its in vivo bioavailability can be improved.

In particular, the present invention provides a pharmaceutical formulation of palbociclib, which comprises a palbociclib free base or a pharmaceutically acceptable salt thereof and an acidic auxiliary material.

In one embodiment, the palbociclib free base or the salt thereof is a solid.

In one embodiment, the particle size (D90) of palbociclib in the pharmaceutical formulation is 20 μm or less.

In one embodiment, the particle size (D90) of palbociclib and the acidic auxiliary material in the pharmaceutical formulation is 20 μm or less.

In one embodiment, the acidic auxiliary material is one or more selected from the group consisting of a pharmaceutically acceptable water-soluble organic acid or a hydrate or an acidic salt thereof, a water-soluble acidic amino acid or a hydrate or an acidic salt thereof, an acidic salt of a water-soluble amino acid or a hydrate thereof, or an acidic salt of a water-soluble inorganic acid or a hydrate thereof.

In one embodiment, the water-soluble organic acid is one or more selected from the group consisting of tartaric acid, fumaric acid, succinic acid, citric acid, lactic acid and malic acid; the water-soluble acidic amino acid is one or more selected from the group consisting of glutamic acid and aspartic acid; the acidic salt of a water-soluble amino acid is one or more selected from the group consisting of the acidic salts of glycine, alanine and serine; and the acidic salt of the water-soluble inorganic acid is one or more selected from the group consisting of dihydric phosphate and bisulfate.

In one embodiment, the acidic auxiliary material is preferably one or more selected from the group consisting of tartaric acid, fumaric acid, succinic acid, citric acid, lactic acid and malic acid, more preferably tartaric acid.

In one embodiment, the mass ratio of the acidic auxiliary material to palbociclib is from 0.2:1 to 5:1, preferably from 0.5:1 to 2:1.

In one embodiment, the pharmaceutical formulation is a tablet or capsule.

In one embodiment, the dosage of the tablet or capsule is from 25 mg to 500 mg, preferably from 50 mg to 150 mg.

The present invention also provides a solid dispersion of palbociclib, which comprises a palbociclib free base or a pharmaceutically acceptable salt thereof, an acidic auxiliary material and a hydrophilic high-molecular weight material.

In one embodiment, the hydrophilic high-molecular weight material is one or more selected from the group consisting of povidone K30 (PVP-K30), copovidone VA64 (PVP-VA64), Soluplus, hydroxypropylmethylcellulose E5 (HPMC-E5), hydroxypropylmethylcellulose acetate succinate (HPMC-AS-HF), hydroxypropyl-β-cyclodextrin and sulfobutylether-β-cyclodextrin.

In one embodiment, the acidic auxiliary material is selected from one or more pharmaceutically acceptable organic acids and optionally one or more pharmaceutically acceptable inorganic acids. Among them, the pharmaceutically acceptable organic acid is preferably selected from the group consisting of tartaric acid, fumaric acid, succinic acid, citric acid, lactic acid, malic acid, aliphatic sulfonic acids (e.g., methanesulfonic acid, ethanesulfonic acid, isethionic acid, etc.) and aromatic sulfonic acids (e.g., benzenesulfonic acid, p-toluenesulfonic acid, etc.), and the pharmaceutically acceptable inorganic acid is preferably selected from the group consisting of hydrochloric acid, sulfuric acid, phosphoric acid and the like. In the present invention, "optionally" means that the pharmaceutically acceptable inorganic acid can be present or absent and, if the pharmaceutically acceptable inorganic acid is present, the amount of the pharmaceutically acceptable organic acid can be reduced.

In one embodiment, the mass ratio of the hydrophilic high-molecular weight material to palbociclib is from 0.1:1 to 10:1, and the mass ratio of the acidic auxiliary material to palbociclib is from 0.2:1 to 5:1; preferably, the mass ratio of the hydrophilic high-molecular weight material to palbociclib is from 1:1 to 3:1, and the mass ratio of the acidic auxiliary material to palbociclib is from 0.5:1 to 2:1.

The present invention also provides a method for the preparation of a pharmaceutical formulation, comprising: mixing an API of palbociclib with a pharmaceutically acceptable acidic auxiliary material, preferably at a certain mass ratio, and further, optionally adding another pharmaceutically acceptable excipient.

The present invention also provides another method for the preparation of a pharmaceutical formulation, comprising: pulverizing the API of palbociclib to control the particle size at 20 μm or less, and then mixing with the pharmaceutically acceptable acidic auxiliary material, or adding the acidic auxiliary material to the API, mixing and co-pulverizing to control the particle size at 20 μm or less; and further, optionally adding another pharmaceutically acceptable excipient.

The present invention also provides a method for the preparation of a solid dispersion, comprising: mixing palbociclib with an acidic auxiliary material; adding a solvent (including but not limited to water, ethanol, acetone and a mixture thereof, preferably water or a mixture thereof with other solvents, e.g. the mixture of water and ethanol, the mixture of water and acetone, etc.) for dissolving or dispersing; adding a hydrophilic high-molecular weight material, dissolving or dispersing evenly; and removing the solvent by heating, for example, evaporating the solvent to dry by vacuum drying or heating drying or freeze drying or other drying ways, in order to achieve the purpose of dispersing the drug in the high-molecular solid carrier to a high degree, so as to prepare the solid dispersion.

In the preparation of the solid dispersion of the present invention, the concentration of the API of palbociclib in the solvent (e.g., water) can be up to 50 mg/ml or more, thereby improving the preparation efficiency of the solid dispersion.

The present invention also provides the use of a pharmaceutical formulation or a solid dispersion for the treatment of breast cancer.

In the present invention, palbociclib refers to a palbociclib free base or a pharmaceutically acceptable salt thereof, which can be used interchangeably.

For those skilled in the art, the excipient is well known and may be an adhesive, a filler, a disintegrant, a lubricant, a preservative, an antioxidant, a flavoring agent, a fragrance, a cosolvent, an emulsifier, a solubilizer, an osmotic pressure regulator, a coloring agent and the like.

In the present invention, palbociclib is pulverized, or the palbociclib is mixed with the acidic auxiliary material and co-pulverized, for example, by means of the airflow pulverization technique, in order to reduce the particle size to D90 at 20 μm or less.

In the present invention, the pharmaceutical formulation is an oral solid formulation product, such as a tablet or a capsule. Such a product is generally prepared by mixing the API with another pharmaceutically acceptable auxiliary material, such as an excipient, a lubricant, a disintegrant and the like, so as to prepare the oral solid formulation product. The palbociclib oral solid formulation product which has been approved for sale in the United States (the trade name is Ibrance), was manufactured by the above-mentioned technique, according to the description in its drug instructions.

The present invention successfully prepares the solid dispersion of palbociclib for the first time by means of a special combination. In the prior art, the solid dispersion is a kind of formulation technique, and useful for a formulation product of an insoluble drug. Usually, an amorphous solid dispersion is prepared from the insoluble API together with a hydrophilic pharmaceutical high-molecular auxiliary material. The methods for the preparation of the amorphous solid dispersion include a solvent method and a melting method. The solvent method includes dissolving the API and the auxiliary material together in a solvent and then volatilizing the solvent. The melting method includes co-melting the API and the high-molecular auxiliary material and rapidly cooling the same. In view of the high melting point of palbociclib, reaching 271° C., and the insolubility in most of solvents, it is impossible to prepare the amorphous solid dispersion in accordance with the solid dispersion technique in the prior art.

Figure 1:
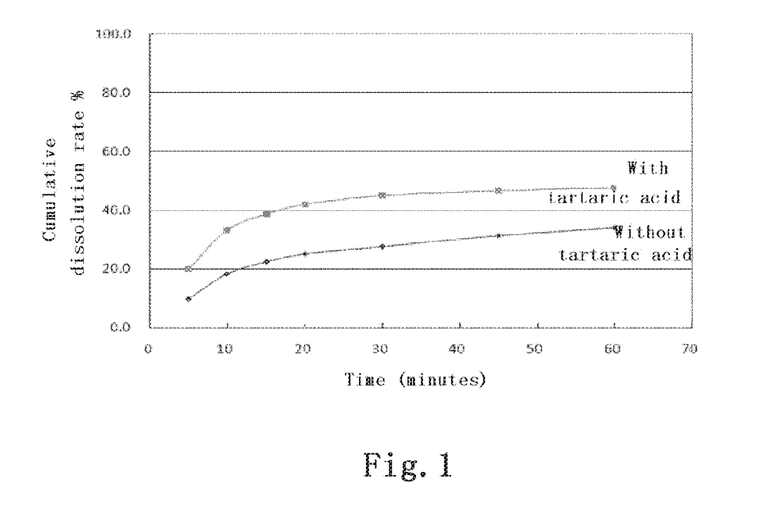
FIG. 1 shows the in vitro dissolution of the capsule formulation prepared from palbociclib with the acidic auxiliary material or without the acidic auxiliary material.

In the present invention, the formulation prepared by mixing the API of palbociclib with the acidic auxiliary material exhibits a cumulative dissolution rate of 47.8% in a dissolution medium at pH 6.0 for 60 minutes, increased from 34.0% of the product prepared by the prior formulation technique (FIG. 1).

Figure 2:
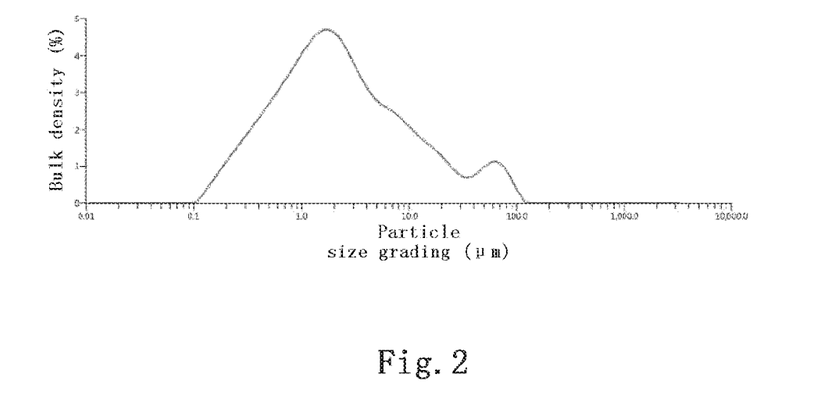
FIG. 2 shows the particle size of the pulverized palbociclib.
Figure 3:
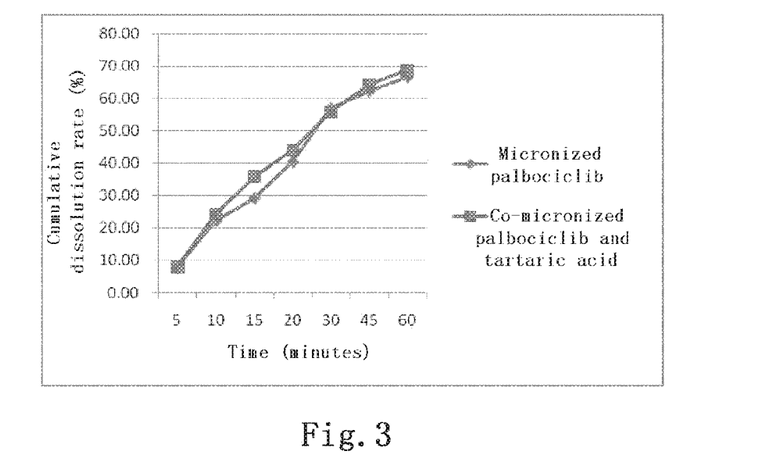
FIG. 3 shows the in vitro dissolution of the capsule formulation prepared by mixing the pulverized palbociclib with the acidic auxiliary material, and of the capsule formulation prepared by co-pulverizing the API of palbociclib and tartaric acid to reduce the particle size.

Further, the formulation prepared by pulverizing palbociclib (having a particle size at 20 μm or less, FIG. 2), or the formulation prepared by mixing and co-pulverizing palbociclib and the acidic auxiliary material exhibits a further increased cumulative dissolution rate of 66.6% and 68.7%, respectively, at pH 6.0 for 60 minutes (FIG. 3).

Figure 4:
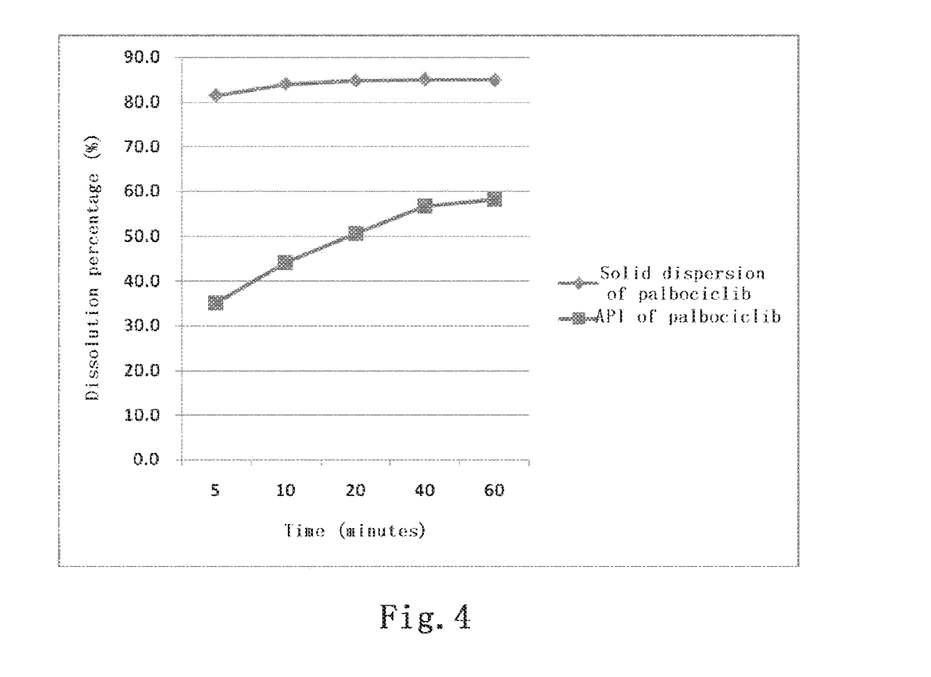
FIG. 4 shows the dynamic solubility of the solid dispersion prepared by mixing the API of palbociclib with the acidic material and then with a hydrophilic high-molecular weight material, compared to the API of palbociclib itself, as tested in a buffer at pH 6.0 with stirring for 60 minutes.

Further, the solid dispersion prepared by mixing the API of palbociclib with the acidic material and then with the hydrophilic high-molecular weight material, exhibits a dynamic solubility of 85%, increased from 58% of the API of palbociclib itself, as shown in a dynamic solubility test performed in a buffer at pH 6.0 with stirring for 60 minutes (FIG. 4).

Figure 5:
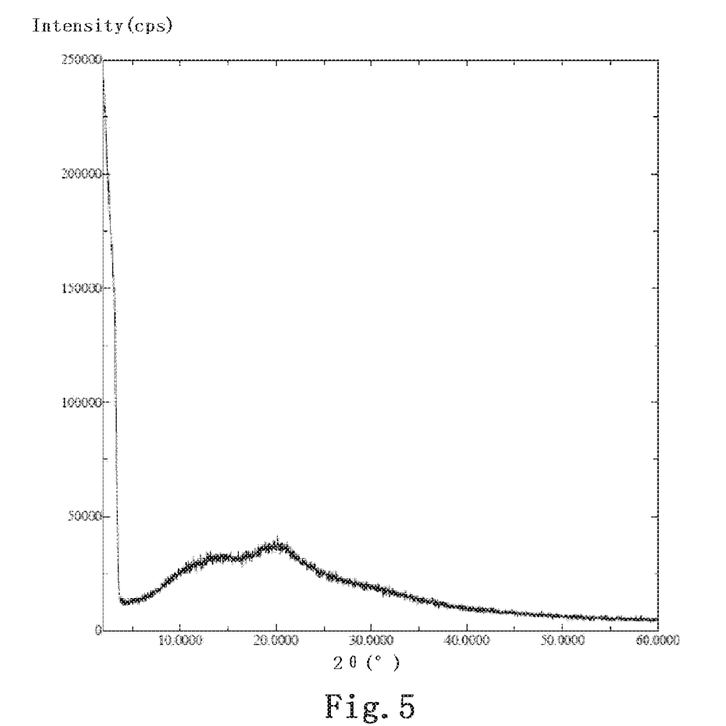
FIG. 5 shows the amorphous state of the acidic auxiliary material tartaric acid in the solid dispersion of the present invention.

The preparation method of the solid dispersion of the present invention can also convert the acidic auxiliary material such as tartaric acid into an amorphous state (FIG. 5) and the amorphous state is maintained over one week of storage in a stabilizing box at 40° C./75% RH, which is advantageous for maintaining the amorphous state of the palbociclib solid dispersion for a long period of time.

DESCRIPTION OF DRAWINGS

In order to clearly describe the technical solutions of the present invention, a brief description will be given below with reference to the drawings. It is apparent that these drawings merely represent some specific embodiments described in the present application. The invention includes, but not limited to, the following drawings.

DESCRIPTION OF EMBODIMENTS

To further understand the present invention, preferred embodiments of the present invention will be described below with reference to examples. These descriptions are merely illustrative for features and advantages of the novel pharmaceutical formulation of the present invention, without limiting the scope of the present invention.

Example 1

Preparation of the Capsule Dosage Form from the Acidic Auxiliary Material and Palbociclib by dry Granulation and Filling 1500 mg of the API of palbociclib, 345 mg of lactose, 1200 mg of tartaric acid, 840 mg of microcrystalline cellulose, 210 mg of sodium carboxymethyl starch and 84 mg of silica were weighed and mixed in a three dimensional mixer for 15 minutes, then 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured at pH 6.0 and at the selected time points of 5, 10, 15, 20, 30, 45 and 60 minutes.

At the same time, a comparative test without the acidic auxiliary material was performed in parallel. 1500 mg of the API of palbociclib, 1545 mg of lactose, 840 mg of microcrystalline cellulose, 210 mg of sodium carboxymethyl starch and 84 mg of silica were weighed and mixed in a three dimensional mixer for 15 minutes, then 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured by a basket method at pH 6.0, at a rotation speed of 100 rpm and at the selected time points of 5, 10, 15, 20, 30, 45 and 60 minutes.

The measurement results of the dissolution of the capsules with the acidic auxiliary material and without the acidic auxiliary material were illustrated by the two curves in FIG. 1 respectively.

Example 2

Preparation of a capsule by mixing the acidic material with palbociclib, followed by pulverization, and dry granulation and filling 1500 mg of the API of palbociclib, which had been pulverized by airflow, was weighed and mixed with 1200 mg of tartaric acid, 345 mg of lactose, 840 mg of microcrystalline cellulose, 210 mg of sodium carboxymethyl starch and 84 mg of silica in a three dimensional mixer for 15 minutes. Then, 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured by a basket method at pH 6.0, at a rotation speed of 100 rpm and at the selected time points of 5, 10, 15, 20, 30, 45 and 60 minutes. The airflow co-pulverized mixture of the API of palbociclib and tartaric acid (comprising 1500 mg of palbociclib and 1200 mg of tartaric acid) was added with 345 mg of lactose, 840 mg of microcrystalline cellulose, 210 mg of sodium carboxymethyl starch and 84 mg of silica, and mixed in a three dimensional mixer for 15 minutes. Then, 21 mg of magnesium stearate was added and mixed for another 2 minutes in the three dimensional mixer. After mixing, the mixture was passed through a 40-mesh sieve and tableted with a mechanical single-punch tableting machine at a pressure of 5 MPa, each tablet weighing 1050 mg. The pressed large tablets were crushed and passed through a 10-mesh sieve, and dispensed into gelatin capsules at a loading of 350 mg per capsule. The dissolution rate was measured by a basket method at pH 6.0, at a rotation speed of 100 rpm and at the selected time points of 5, 10, 15, 20, 30, 45 and 60 minutes. The dissolution results of the formulation prepared by pulverizing palbociclib alone and of the formulation prepared by co-pulverizing palbociclib and tartaric acid were shown in FIG. 3.

Example 3

Preparation of a Solid Dispersion by Mixing Palbociclib with the Acidic Material and then with PVP-K30

100 mg of the API of palbociclib and 200 mg of tartaric acid were weighed and placed into a 10 ml penicillin bottle, added with 2 ml of purified water, mixed and dissolved. 200 mg of PVP-K30 (manufactured by BASF, Germany, full name: povidone K30) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 4

Preparation of a Solid Dispersion by Mixing Palbociclib with the Acidic Material and then with a Solid Carrier PVP-VA64

100 mg of the API of palbociclib and 200 mg of tartaric acid were weighed and placed into a 10 ml penicillin bottle, added with 2 ml of double distilled water, mixed and dissolved. 200 mg of PVP-VA64 (manufactured by BASF, Germany, full name: Copovidone) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight for 18 hours at 40° C., and removed the next day, and thereby, the solid dispersion was prepared.

Example 5

Preparation of a Solid Dispersion by Mixing Palbociclib with the Acidic Material and then with a Solid Carrier Soluplus 100 mg of the API of palbociclib and 200 mg of tartaric acid were weighed and placed into a 10 ml penicillin bottle, added with 2 ml of double distilled water, mixed and dissolved. 200 mg of Soluplus (manufactured by BASF, Germany, full name: polyethylene caprolactam-polyvinyl acetate-polyethylene glycol graft copolymer) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 6

Preparation of a Solid Dispersion by Mixing Palbociclib with the Acidic Material and then with a Solid Carrier HPMC-E5

100 mg of the API of palbociclib and 200 mg of tartaric acid were weighed and placed into a 10 ml penicillin bottle, added with 2 ml of double distilled water, mixed and dissolved. 200 mg of HPMC-E5 (manufactured by BASF, Germany, full name: hydroxypropylmethylcellulose E5) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 7

Preparation of a Solid Dispersion by Mixing Palbociclib with the Acidic Material and then with a Solid Carrier HPMC-AS-HF 100 mg of the API of palbociclib and 200 mg of tartaric acid were weighed and placed into a 10 ml penicillin bottle, added with 2 ml of double distilled water, mixed and dissolved. 200 mg of HPMC-AS-HF (manufactured by BASF, Germany, full name: hydroxypropylmethylcellulose AS-HF) was added to the solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 8

Preparation of a Solid Dispersion by Mixing Palbociclib with the Acidic Material and Hydrochloric Acid and then with a Solid Carrier PVP VA64

125 mg of the API of palbociclib was weighed and placed into a 10 ml penicillin bottle; 1.991 ml of double distilled water and 8.63 μl of 36% hydrochloric acid solution (having a density of 1.18 g/mL) were added, so that the molar ratio of hydrochloric acid to the API of palbociclib was 1:1. Then 200 mg of tartaric acid was added and completely mixed and dissolved under the action of ultrasound. 100 mg of PVP VA64 was added to the above solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 9

Preparation of a Solid Dispersion by Mixing Palbociclib with the Acidic Material and Phosphoric Acid and then with a Solid Carrier PVP VA64

125 mg of the API of palbociclib was weighed and placed into a 10 ml penicillin bottle; 2 ml of double distilled water and 27.3 mg of phosphoric acid were added, so that the molar ratio of phosphoric acid to the API of palbociclib was 1:1. Then 200 mg of tartaric acid was added and completely mixed and dissolved under the action of ultrasound. 100 mg of PVP VA64 was added to the above solution and dissolved by ultrasound together with hand shaking. In a fume hood, water was volatilized by means of stirring under heating; and nitrogen was introduced to facilitate water evaporation. Stop heating and stirring when the content of the penicillin bottle was gelatinous and there was no more liquid reduction. It was placed into a vacuum dryer, overnight at 40° C., and removed the next day, and thereby, the solid dispersion was prepared.

Example 10

Figure 6:
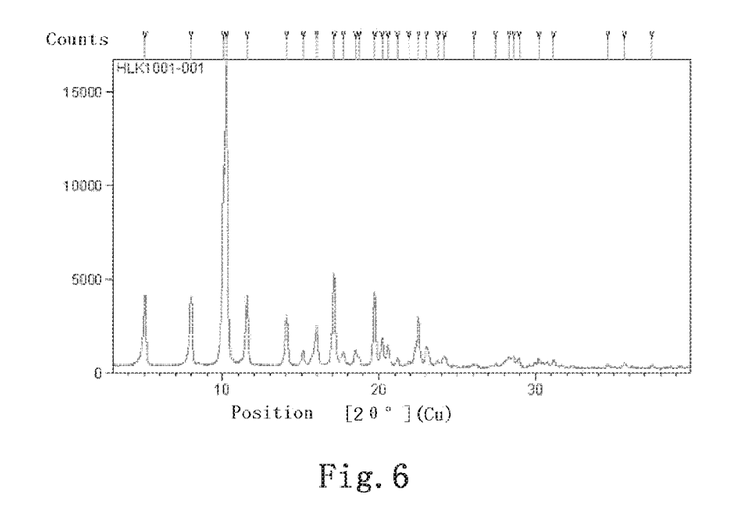
FIG. 6 shows an XRPD pattern of the API of palbociclib used in the present invention.
Figure 9:
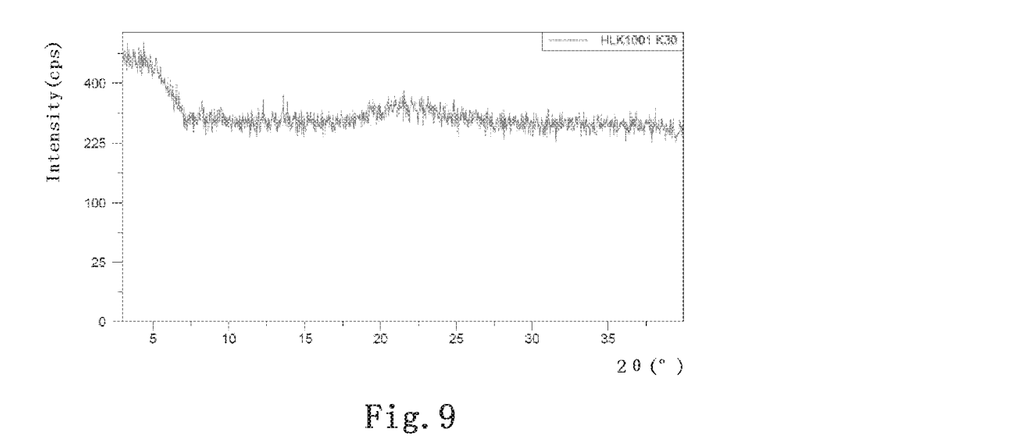
FIG. 9 shows an XRPD pattern of a palbociclib solid dispersion prepared with PVP-K30.

The palbociclib solid dispersion prepared with PVP-K30 in Example 3 and the API of palbociclib both were sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°): 0.0263; scanning time (seconds): 46.665; K-Alpha wavelength (Å): 1.54060; K-Alpha2 wavelength (Å): 1.54443; Power setting: 40 mA, 45 kV. The obtained XRPD pattern of the API of palbociclib was shown in FIG. 6; and the XRPD pattern of the solid dispersion prepared with PVP-K30 was shown in FIG. 9.

Example 11

Figure 8:
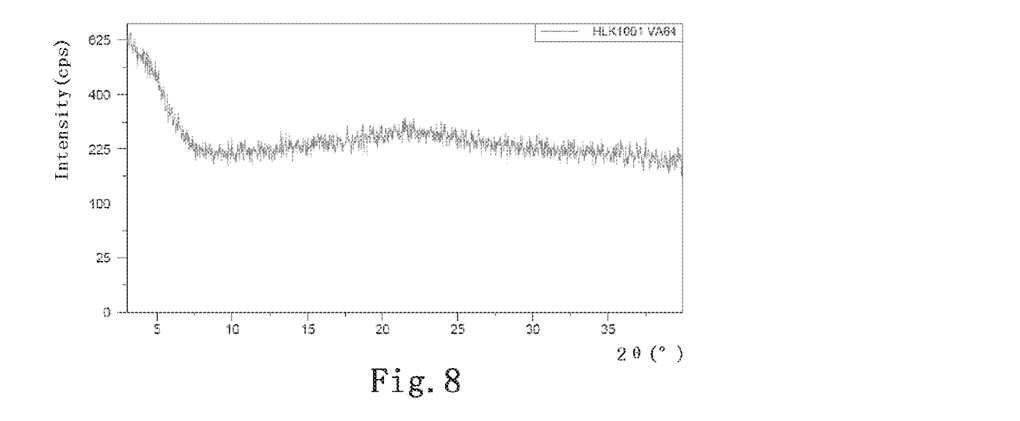
FIG. 8 shows an XRPD pattern of a palbociclib solid dispersion prepared with PVP-VA64.

The palbociclib solid dispersion prepared with PVP-VA64 in Example 4 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 8.

Example 12

Figure 10:
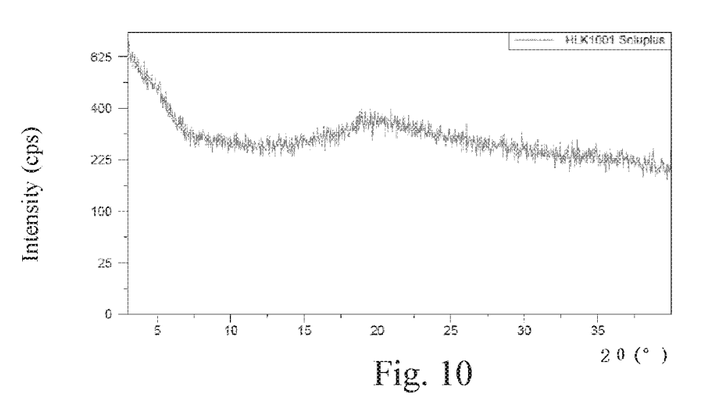
FIG. 10 shows an XRPD pattern of a palbociclib solid dispersion prepared with Soluplus.

The palbociclib solid dispersion prepared with Soluplus in Example 5 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 10.

Example 13

Figure 11:
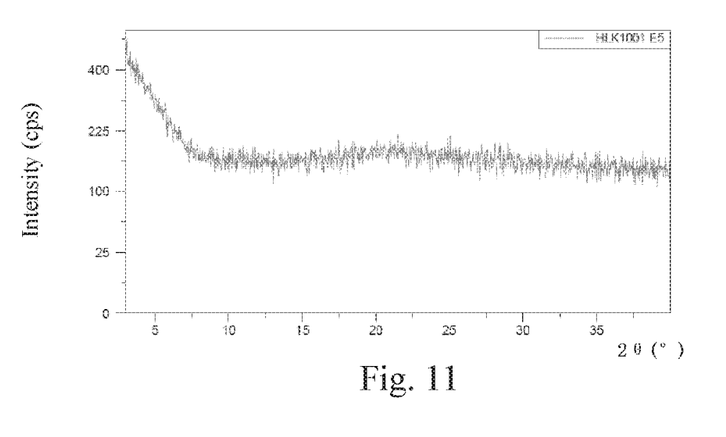
FIG. 11 shows an XRPD pattern of a palbociclib solid dispersion prepared with HPMC-E5.

The solid dispersion prepared with HPMC-E5 in Example 6 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 11.

Example 14

Figure 7:
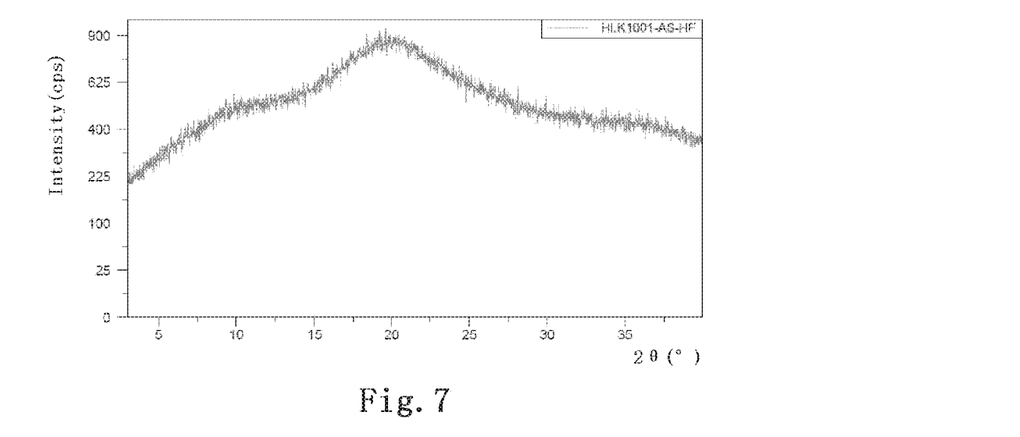
FIG. 7 shows an XRPD pattern of a palbociclib solid dispersion prepared with HPMC-AS-HF.

The solid dispersion prepared with HPMC-AS-HF in Example 7 was sent for XRPD test. The XRPD test was performed with Panalytical's XPERT-3 X-ray diffractometer. About 10 mg of sample was evenly tiled on a monocrystalline silicon sample tray and subjected to the XRPD test with the following parameters: scanning range (2θ°): 3-40; scanning step (2θ°):0.0263; scanning time (seconds): 46.665; K-Alpha wavelength (Å): 1.54060; K-Alpha2 wavelength (Å): 1.54443; Power setting: 40 mA, 45 kV. The obtained XRPD pattern was shown in FIG. 7.

Example 15

62.5 mg of the solid dispersion prepared in Example 3 (containing 12.5 mg of the API of palbociclib in proportion) and 12.5 mg of the API of palbociclib were weighed separately, placed into two 100 ml beakers, respectively, and marked with T1 and T2. 90 ml of phosphate buffer (pH 6.0) was added to the two beakers respectively and a magnetic stir bar was placed therein. The two beakers were placed on a magnetic stirrer separately. 1 ml of the solution was removed separately from each of the beakers at the time points of 5, 10, 20, 40, and 60 minutes and filtered through a 0.45 μm micro PES polyethersulfone filter membrane. The filtrate was analyzed by high performance liquid chromatography, the content of the API of palbociclib was determined and the dissolution percentage was calculated. The results were shown in FIG. 4.

The description of the above examples is only intended to help understanding the central concept of the present invention. It should be noted that those skilled in the art may make improvements and modifications to the novel formulation and its preparation method according to the present invention without departing from the principles of the present invention, and such improvements and modifications also fall within the scope of protection of the claims in the present invention.

The invention claimed is:

1. A single amorphous solid dispersion, wherein the single amorphous solid dispersion comprises:
   palbociclib or a pharmaceutically acceptable salt thereof;
   tartaric acid; and
   a hydrophilic high-molecular weight material, wherein a mass ratio of the tartaric acid to the palbociclib or the pharmaceutically acceptable salt thereof ranges from 0.5:1 to 5:1, wherein the palbociclib and the tartaric acid are dispersed within the hydrophilic high-molecular weight material; and wherein the palbociclib and tartaric acid are in an amorphous state.

2. The single amorphous solid dispersion according to claim 1, further comprising a pharmaceutically acceptable inorganic acid selected from the group consisting of hydrochloric acid, sulfuric acid, phosphoric acid, and combinations thereof.

3. The single amorphous solid dispersion according to claim 1, wherein the hydrophilic high-molecular weight material is one or more selected from the group consisting of povidone K30, copovidone VA64, Soluplus, hydroxypropylmethylcellulose E5, hydroxypropylmethylcellulose acetate succinate, hydroxypropyl-β-cyclodextrin and sulfobutyl ether-β-cyclodextrin.

4. The single amorphous solid dispersion according claim 1, wherein a mass ratio of the hydrophilic high-molecular weight material to the palbociclib or the pharmaceutically acceptable salt thereof is from 0.1:1 to 10:1.

5. The single amorphous solid dispersion according to claim 4, wherein the mass ratio of the hydrophilic high-molecular weight material to the palbociclib or the pharmaceutically acceptable salt thereof is from 1:1 to 3:1, and the mass ratio of the tartaric acid to the palbociclib or the pharmaceutically acceptable salt thereof is from 0.5:1 to 2:1.

6. A method for preparing the single amorphous solid dispersion according to claim 1, comprising: mixing the palbociclib or the pharmaceutically acceptable salt thereof with the tartaric acid, adding a solvent for dissolving or dispersing, adding the hydrophilic high-molecular weight material, dissolving or dispersing evenly, and removing the solvent by heating.

7. The method according to claim 6, wherein the concentration of the palbociclib or the pharmaceutically acceptable salt thereof in the solvent is 50 mg/ml or more.

8. The method according to claim 6, wherein the concentration of the palbociclib or the pharmaceutically acceptable salt thereof in the solvent is up to 50 mg/ml.

* * * * *